Figure 1:
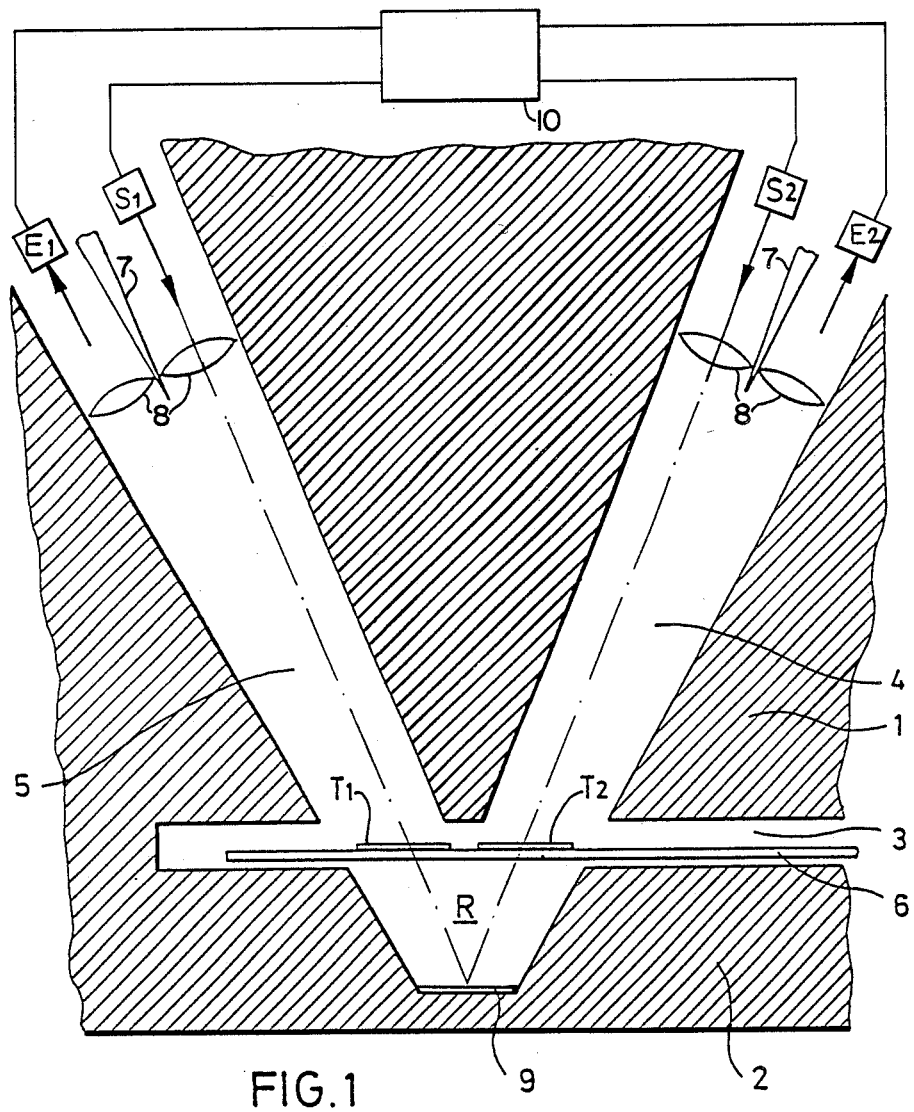

United States Patent [19]

Gassenhuber et al.

[11] Patent Number: 4,894,552

[45] Date of Patent: Jan. 16, 1990

[54] DIFFERENTIAL-REFLECTANCE PHOTOMETER

[75] Inventors: Helmut Gassenhuber, Starnberg; Walter Ziegler, Munich, both of Fed. Rep. of Germany

[73] Assignee: LRE Relais & Elektronik GmbH, Munich, Fed. Rep. of Germany

[21] Appl. No.: 228,260

[22] Filed: Aug. 4, 1988

[30] Foreign Application Priority Data

Aug. 21, 1987 [DE] Fed. Rep. of Germany ....... 8711377

[51] Int. Cl.$^4$ ............................................. G01N 21/88
[52] U.S. Cl. ..................................... 250/572; 356/222
[58] Field of Search ................ 250/571, 572; 356/213, 356/217, 218, 222, 445; 355/68

[56] References Cited

U.S. PATENT DOCUMENTS 4,249,081  2/1981  Cole et al. ........................... 250/572
4,639,592  1/1987  Heitmann ............................ 250/572

Primary Examiner—David C. Nelms
Assistant Examiner—William L. Oen

[57] ABSTRACT

The invention concerns a differential-reflectance photometer for quantitatively evaluating test strips, especially for chemical analysis. The differential-reflectance photometer is characterized in that two optical channels are arranged in one housing in V-shaped fashion with each channel receiving an optical emitting and an optical receiving arrangement, that the channels enter a common space at the apex of the V, that a reference field associated with both emitting and receiving arrangement is provided on the bottom of the common space, that the emitting and receiving arrangements are connected to a common evaluation apparatus, and in that between the reference field and the emitting and receiving arrangements is a receiving slot, which intersects both channels, for receiving a test strip with two test fields each of which becomes associated with a respective one of the two channels.

3 Claims, 1 Drawing Sheet

DIFFERENTIAL-REFLECTANCE PHOTOMETER

The invention concerns a differential-reflectance photometer for quantitatively evaluating test strips, especially for chemical analysis. A reflectance photometer with double optics, with which the two fields of a test strip can be measured independently of one another, is already known. In it however, both optical channels have to be calibrated independently of one another with a brigthness standard. In order to be able to measure the smallest difference, for example in the comparison of a test field with a reference field of a test strip, it is necessary that both optical channels be calibrated with the same standard. This poses the requirement that the reference field used as a standard remain constant and unchanging for a long time forward.

The invention has as its object, the provision of a differential-reflection photometer of the type mentioned above, but in which a calibration of the two optical measuring branches can be carried out in a simple way and with simple means.

This object is solved in accordance with the invention in that two optical channels are arranged in one housing in V-shaped fashion with each channel receiving an optical emitting and an optical receiving arrangement, that the channels enter a common space at the apex of the V, that a reference field associated with both emitting and receiving arrangements is provided on the bottom of the common space, that the emitting and receiving arrangements are connected to a common evaluation apparatus, and in that between the reference field and the emitting and receiving arrangements is a receiving slot, which intersects both channels, for receiving a test strip with two test fields each of which becomes associated with a respective one of the two channels.

While in known arrangements the previous calibration of the optical measuring apparatus was carried out with two different standard surfaces, during which upon the insertion of a normal or standard strip in place of the test strip a fault in the normal strip can lead to a measurement error, in the case of the invention the same field is used to calibrate both optical measuring branches. Therefore, for example, errors can be eliminated which arises from the fact that different soiling or different aging of the standard surfaces lead to a different calibration of the optical branches. With this, moreover, there is also avoided the problem of previous reflectance photometers that the normal or reference field must remain constant during the period of operation. Especially, the previous customary large expense of calibrating with a calibration standard made of pressed barium sulfide need no longer be borne.

The receiving slot can be closed at one of its ends, so that upon the insertion of a test strip a stop is provided which assures the test fields on the test strip being positioned exactly in the channels intended for them.

The optical emitting and receiving arrangements are for example so formed that each emitter is separated with its cooperating receiver in the associated channel.

Figure 2:
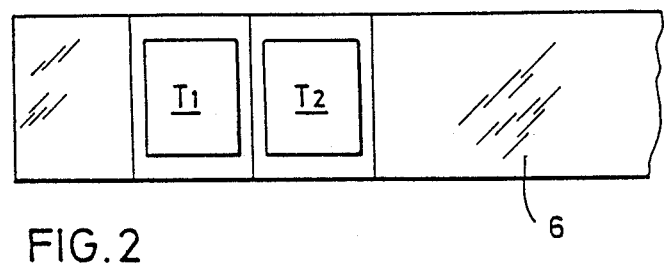

The following description explains the invention in connection with the accompanying drawings in connection with an exemplary embodiment. The drawings show:

FIG. 1a schematic partial section through a differential reflectance photometer embodying the invention, and FIG. 2a plan view of a test strip insertable in the reflectance photometer of FIG. 1.

FIG. 1 shows a housing 1 with a lower part 2 in which two channels 4 and 5 are provided, which channels are arranged in the form of a V and which in the area of the apex of the V enter a common space 9. In each channel 4 and 5 is an emitter S1 or S2 and a cooperating receiver E1 or E2, with each emitter S1 or S2 being separated from its associated receiver E1 or E2 by a separating wall 7. The emitters S1 and S2 as well as the receivers E1 and E2 can each be associated with an optical system which is schematically illustrated by a lens 8. The receivers E1 and E2 are connected to an electronic computer 10 for comparing and evaluating the measured photometric values.

A reference field R is provided on the bottom surface of the space 9. Parallel to this bottom surface or to the reference field R, and between this and the optical emitting and receiving arrangements S1, E1 and S2, E2 is an elongated receiving slot 3 formed in the housing 1, which slot is closed at one of its ends. A test strip 6 is insertable in this receiving slot, the strip having two separate test fields T1 and T2, as especially seen in FIG. 2. These test fields T1 and T2 are so arranged on the test strip 6 that after the insertion they are positioned exactly and respectively in the channels 5 and 4 and are turned toward the optical emitting and receiving arrangements S1, E1 and S2, E2, so that the test fields can be measured by these arrangements.

So long as no test strip is inserted in the receiving slot 3, the emitteer S1 and/or the emitter S2 illuminates the reference field R. The receiver E1 receives the reflected light of the emitter S1 from the same reference field R as is the case with the receiver E2 and the light emitted by the emitter S2. In operation the two emitters S1 and S2 are alternately switched on and off so that the reference field R is first measured through one channel and subsequently measured through the other channel. The electronic evaluation device 10 connected to the receivers E1 and E2 sets the measured values equal to one another, so that the absolute value of the reference field as measured in both channels is non-essential. In this way there results a calibration of the optical system in both of the channels 4 and 5. Subsequently, the test strip 6 is inserted into the apparatus, until it abuts against the closed end of the receiving slot 3. In this position the test fields T1 and T2 lie in the channels 4 and 5 respectively and can be measured independently of one another by the optical emitting and receiving arrangements S1, E1 and S2, E2. Very small reflectance differences between the test fields T1 and T2 lead to different signals, so that the smallest difference between the test field T1 and T2 is recognizable and measurable.

As an example of use, a chemical investigation of water is mentioned in the following.

For example, the nitrite content of water can be determined. For this the test strip is dipped into the water under investigation, as a result of which the two test fields become differently colored, because one test field is provided with a reagent which discolors because of a chemical reaction with the nitrite, whereas the other test field becomes solely saturated and dulled by the, in certain circumstances dirty, water. The difference in the coloration is measured, in which case the measured difference between the rays proceeding away from the two test fields is a measure of the different chemical reaction on the two test fields. Therefore, from the different coloration of the two test fields, by the corresponding evaluation of the signals produced by the two receivers E1 and E2, the amount of the investigated substance in the water can be determined.

We claim:

1. A differential-reflectance photometer for quantitatively evaluating test strips, especially for chemical analysis, characterized in that two channels, each containing an optical emitter and receiving arrangement, are provided in a housing and are arranged to form a V, that at the apex of the V the two channels enter a common space, that on the bottom of the common space is provided a reference field associated with both of the optical emitting and receiving arrangements, that the two optical emitting and receiving arrangements are connected with a common evaluating apparatus, and that between the reference field and the emitting and receiving arrangements of the two channels is a receiving slot for a test strip having two test fields associated respectively with the channels and which receiving slot intersects both of the channels, whereby when a test strip is positioned in said slot each of said two optical emitting and receiving arrangements is responsive to the light reflected from the associated one of said two test fields and whereby when a test strip is not positioned in said slot each of said two optical emitting and receiving arrangements is responsive to the light reflected from said reference field.

2. A differential-reflectance photometer according to claim 1, further characterized in that each emitter is separated in its channel from its associated receiver.

3. A differential-reflectance photometer according to claim 1 or 2, characterized in that the slot is closed at one of its ends.

* * * * *